US011517510B2

(12) United States Patent
Yeung et al.

(10) Patent No.: US 11,517,510 B2
(45) Date of Patent: Dec. 6, 2022

(54) HAND SANITIZER AND METHOD OF MAKING THE SAME

(71) Applicants: CHIAPHUA INDUSTRIES LIMITED, Hong Kong (CN); GERMAGIC BIOCHEMICAL TECHNOLOGY (SHANGHAI) CO., LTD., Shanghai (CN)

(72) Inventors: King Lun Yeung, Hong Kong (CN); Ying Li, Hong Kong (CN); Ning Zhan, Hong Kong (CN)

(73) Assignee: GERMAGIC BIOCHEMICAL TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 16/518,154

(22) Filed: Jul. 22, 2019

(65) Prior Publication Data
US 2021/0022969 A1    Jan. 28, 2021

(51) Int. Cl.
| | |
|---|---|
| *A61K 8/04* | (2006.01) |
| *A61Q 19/10* | (2006.01) |
| *A61K 8/11* | (2006.01) |
| *A61K 8/9789* | (2017.01) |
| *A61K 8/67* | (2006.01) |
| *A61K 8/73* | (2006.01) |
| *A61K 8/84* | (2006.01) |
| *A61K 8/46* | (2006.01) |

(52) U.S. Cl.
CPC ............... *A61K 8/11* (2013.01); *A61K 8/046* (2013.01); *A61K 8/463* (2013.01); *A61K 8/676* (2013.01); *A61K 8/678* (2013.01); *A61K 8/735* (2013.01); *A61K 8/84* (2013.01); *A61K 8/9789* (2017.08); *A61Q 19/10* (2013.01)

(58) Field of Classification Search
None
See application file for complete search history.

(56) References Cited

U.S. PATENT DOCUMENTS

| | | | |
|---|---|---|---|
| 7,803,746 B2 * | 9/2010 | Luu ........................ | A61Q 19/10 510/156 |
| 2008/0051314 A1 * | 2/2008 | Wenzel .................... | A61K 8/11 510/507 |
| 2019/0174749 A1 * | 6/2019 | Yeung .................... | A01N 25/10 |

* cited by examiner

*Primary Examiner* — H. Sarah Park
(74) *Attorney, Agent, or Firm* — Nath, Goldberg & Meyer; Jerald L. Meyer; Morgan D. Rosenberg

(57) ABSTRACT

The hand sanitizer may be a hand foam sanitizer or a hand gel sanitizer. Each of the hand sanitizers includes at least one stabilizing agent, at least one skin care agent, and a volume of disinfecting micelle capsules suspended therein. Each disinfecting capsule has a polymer shell which defines a hollow core. The polymer shell includes an antimicrobial material. The antimicrobial material may have a concentration of between 0.5 wt % and 95 wt % of the polymer shell. In order to make the hand foam sanitizer, at least one foaming agent is added to produce a foam by air foaming. The hollow core of each disinfecting capsule may be filled with a material, such as at least one disinfectant, at least one fragrance, at least one supplemental skin care agent, or combinations thereof.

15 Claims, 5 Drawing Sheets

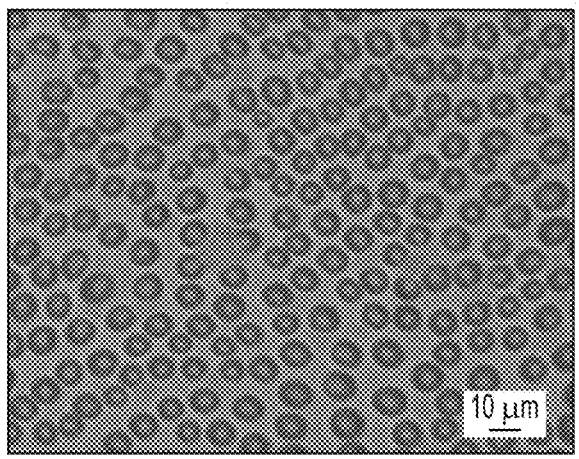
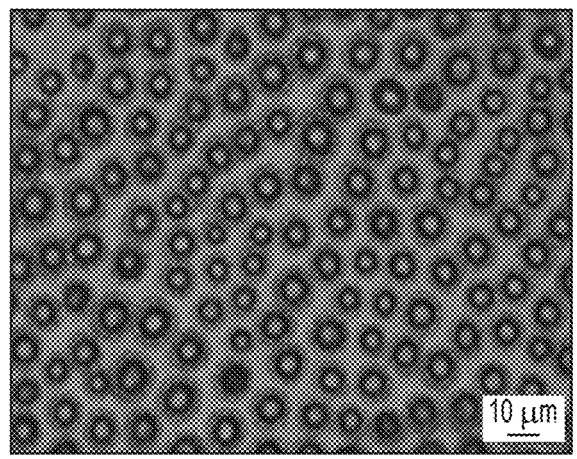
FIG. 1A  FIG. 1B
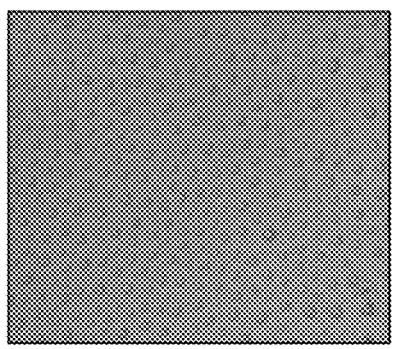
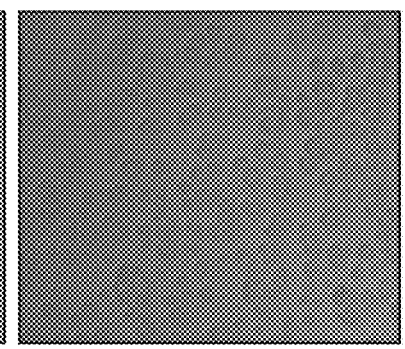
FIG. 2A  FIG. 2B  FIG. 2C
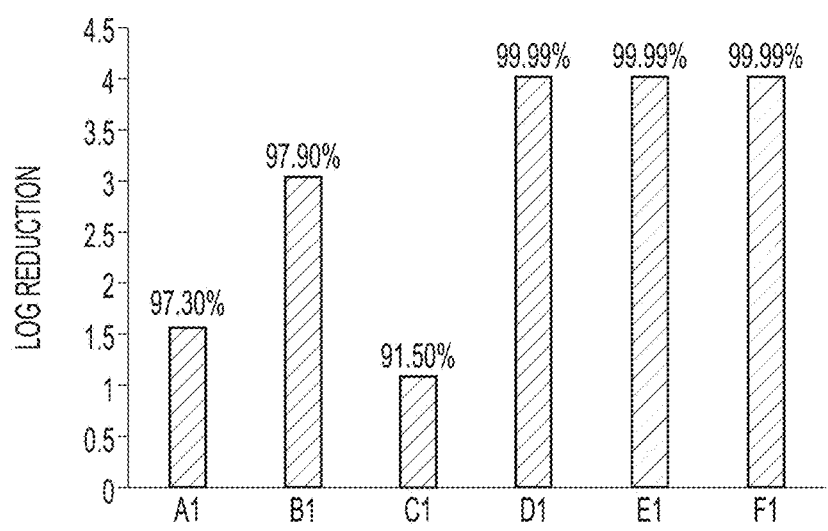
FIG. 3

HAND SANITIZER AND METHOD OF MAKING THE SAME

BACKGROUND

1. Field

The disclosure of the present patent application relates to disinfectants, and particularly to hand foam sanitizers and hand gel sanitizers containing disinfecting capsules.

2. Description of the Related Art

Unclean hands play an important role in the transmission of pathogens. Infection may occur when hands contaminated with pathogens touch the eyes, nose or lips, allowing microorganisms to enter through the mucous membranes thereof. Numerous studies support hand hygiene as being an important factor in reducing the carrying and transmission of pathogens on hands to prevent disease transmission and infection. However, according to the Centers for Disease Control and Prevention (CDC), only about 5% of people wash their hands long enough to destroy infectious germs after using the bathroom.

Although a wide variety of hand washing devices and accessories exist, such as devices to monitor hand washing process or assist in hand washing for periods of about 15 seconds to remove germs, such devices and accessories are not widely used, as they are typically costly and difficult to install. Further, as with conventional washing, there is no certainty that the devices will be used, despite their presence and obvious utility.

The use of both alcohol-based and alcohol-free antimicrobial hand gel and hand foam is another commonly used method for hand disinfection, particularly due to their convenience, low costs, and ease of application. However, alcohol-based hand sanitizers often leave the skin dry, and with repeated use, cause skin irritation. On the other hand, many alcohol-free products leave sticky residue on the skin. Another, disadvantage is that the sanitizers do not last long and disinfection lasts for only a short time. Thus, a hand sanitizer and method of making the same solving the aforementioned problems is desired.

SUMMARY

The hand sanitizer may be a hand foam sanitizer or a hand gel sanitizer. Each of the hand sanitizers includes at least one stabilizing agent, at least one skin care agent, and a volume of disinfecting micelle capsules suspended therein. Each disinfecting capsule has a polymer shell which defines a hollow core. The polymer shell includes an antimicrobial material. The antimicrobial material may have a concentration of between 0.5 wt % and 95 wt % of the polymer shell. In order to make the hand foam sanitizer, at least one foaming agent is added to produce a foam by air foaming. Preferably, the at least one foaming agent and the at least one stabilizing agent are selected to maintain a size and shape of the foam for at least 60 seconds at room temperature (25° C.).

Non-limiting examples of the at least one foaming agent include soap, liquid soap, powdered detergent, liquid detergent, sodium dodecyl sulfate, surfactants, and combinations thereof. Non-limiting examples of the at least one stabilizing agent include nonionic surfactants, emulsifying agents, polysorbate 20, polysorbate 40, polysorbate 80, and combinations thereof. Non-limiting examples of the at least one skin care include at least one moisturizer, at least one skin repair agent, at least one emollient, at least one vitamin, and combinations thereof. As non-limiting examples, the at least one skin care agent may include hyaluronic acid, sodium hyaluronic, vitamin E, ceramides, sodium PCA, glycerin, glycerol, silicones, petrolatum, salicylic acid, alpha hydroxy acids, vitamin C, hyaluronic acid, beta-glucan, shea butter, mineral oil, plant butter, cocoa butter, lanolin, petrolatum, paraffin, beeswax, squalene, cetyl alcohol, triethyhexanoin, vitamin A, vitamin D, vitamin K, vitamin B3, vitamin B5, choline, and combinations thereof.

The polymer shell includes at least one polymer, including, but not limited to, anionic polymers, cationic polymers, nonionic polymers and combinations thereof. Non-limiting examples of the at least one polymer include primary amines, secondary amines, tertiary amines, zwitterionics, quarternary ammoniums, polyethylenimine, polyquarternium, polyhexamethylene biguanide, poly(diallyldimethylammonium chloride, functionalized chitosan, as well as any other suitable polymers with bactericidal, virucidal and sporicidal activities, and combinations thereof.

The hollow core of each disinfecting capsule may be filled with a material, such as at least one disinfectant, at least one fragrance, at least one supplemental skin care agent, or combinations thereof. Non-limiting examples of the at least one disinfectant include alcohol, chlorhexidine, antimicrobial phytochemicals, antimicrobial essential oils, agarwood oil, cajuput oil, cananga oil, cinnamon bark oil, citronella oil, clove oil, eucalyptus oil, fennel oil, ginger oil, kaffir lime oil, nutmeg oil, ollium xanthorrhiza oil, origanum oil, patchouli oil, rosemary oil, sandalwood oil, tea tree oil, thyme oil, vetiver oil and combinations thereof. Non-limiting examples of the at least one fragrance include essential oils of flowers, essential oils of fruits, essential oils of aromatic woods and combinations thereof. Non-limiting examples of the at least one supplemental skin care agent include hyaluronic acid, sodium hyaluronic, vitamin E, ceramides, sodium PCA, glycerin, glycerol, silicones, petrolatum, salicylic acid, alpha hydroxy acids, beta-glucan, mineral oil, plant butters, shea butter, cocoa butter, lanolin, petrolatum, paraffin, beeswax, squalene, cetyl alcohol, triethyhexanoin, vitamin A, vitamin C, vitamin E, vitamin D, vitamin K, vitamin B3, vitamin B5, choline, catechins and combinations thereof.

In order to make the hand sanitizer, an aqueous polymer solution of at least one polymer is mixed with a material to form a mixture. The material may include at least one disinfectant, at least one fragrance, at least one skin care agent, or combinations thereof. The at least one polymer includes an antimicrobial material, and the resultant mixture forms an aqueous solution of the disinfecting capsules. At least one stabilizing agent and at least one skin care agent are mixed with the mixture to form a suspension of the disinfecting capsules in the at least one stabilizing agent and the at least one skin care agent. In order to make the hand foam sanitizer, the mixture is further mixed with at least one foaming agent.

As a further alternative, the hand foam sanitizer may be prepared by providing a skin care ingredient-containing solution separately from a suspension containing the at least one foaming agent and the volume of disinfecting capsules suspended therein. The skin care ingredient-containing solution can then be selectively mixed with the suspension at a desired ratio. It should be understood that the skin care ingredient(s) and foaming agent(s) may be any desired skin care ingredient(s) and foaming agent(s), such as those described with regard to the previous embodiments.

These and other features of the present subject matter will become readily apparent upon further review of the following specification.

BRIEF DESCRIPTION OF THE DRAWINGS

FIG. 1A is a 500× microscope image of disinfecting capsules made from antimicrobial polymer polyethylenimine (PEI) (type A1).

FIG. 1B is a 500× microscope image of disinfecting capsules made from a combination of PEI and polyhexamethylene biguanide (PHMB) (type D1).

FIG. 2A is a 200× microscope image of type D3 disinfecting capsules with no additional surfactant.

FIG. 2B is a 200× microscope image of type D3 disinfecting capsules with 0.1 wt % sodium dodecyl sulfate (SDS) as a surfactant.

FIG. 2C is a 200× microscope image of type D3 disinfecting capsules with 0.2 wt % sodium dodecyl sulfate (SDS) as a surfactant.

FIG. 3 is a graph comparing the bactericidal properties of disinfecting capsules of types A1, B1, C1, D1, E1 and F1 against $10^5$ CFU S. aureus for a contact time of 60 seconds.

Similar reference characters denote corresponding features consistently throughout the attached drawings.

DETAILED DESCRIPTION OF THE PREFERRED EMBODIMENTS

Figure 4:
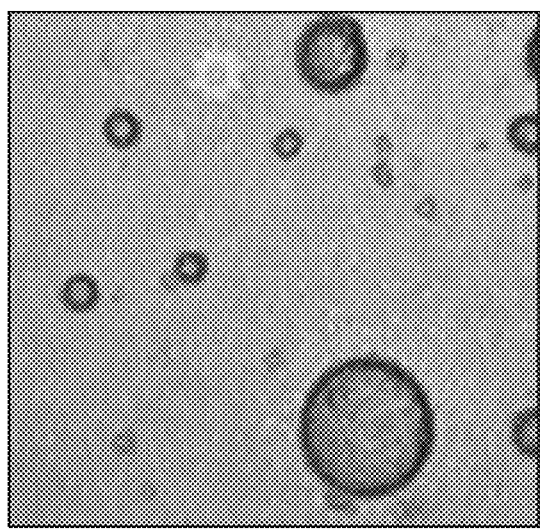
FIG. 4 is a 200× microscope image of a suspension of type A1 disinfecting capsules with thyme oil.

The hand sanitizers include formulations for water-based hand sanitizers, such as hand foams and hand gels, which are effective for killing germs and microbes. The hand sanitizers disinfect by contact-killing, anti-adhesion and/or release-killing, and can further store and release fragrance and skin-care ingredients over time. The hand sanitizers contain disinfecting capsules of micelles structures, which store active disinfectants, fragrances, and/or skin-care ingredients within an encapsulating shell. The shell possesses one or more antimicrobial properties, such as contact-killing, anti-adhesion and/or anti-biofilm. The encapsulating shell also controls the dosing of the stored disinfectants, fragrances and/or skin-care ingredients, thus prolonging their effectiveness. The hand sanitizers provide long-term protection against germs and microorganisms.

The disinfecting micelle capsules include an antimicrobial polymeric shell and a core-space for storing active disinfectants, fragrance and skin-care ingredients that are slow-released to provide long-term performance. The formulations of the hand sanitizers, as will be described in greater detail below, include ingredients such as disinfectants, fragrances, polymers, foaming agents and stabilizers, thickener and viscosity enhancers, and skin-care ingredients that provide moisturizing and/or skin repair and/or emollient and/or vitamin for care of the skin.

The stored disinfectants include, but are not limited to, common disinfectant solutions, such as alcohol, chlorhexidine and other chemical or mineral disinfectants, as well as phytochemicals that exhibit antimicrobial properties, including essential oils and their active antimicrobial components. The essential oils include, but are not limited to, agarwood oil, cajuput oil, cananga oil, cinnamon bark oil, citronella oil, clove oil, eucalyptus oil, fennel oil, ginger oil, kaffir lime oil, nutmeg oil, ollium xanthorrhiza oil, origanum oil, patchouli oil, rosemary oil, sandalwood oil, tea tree oil, thyme oil, vetiver oil or other plant-derived extracts that exhibit antimicrobial properties.

The stored fragrances include, but are not limited to, natural and synthetic essence of flowers, fruits and aromatic woods that are pleasant to smell and provide olfactory pleasure. Fragrance may also be added to provide an olfactory cue for the presence of the disinfection function. The stored skin-care ingredients include, but are not limited to, moisturizers, such as hyaluronic acid, sodium hyaluronic, vitamin E, ceramides, sodium PCA, glycerin, glycerol, silicones, petrolatum, salicylic acid, alpha hydroxy acids and others with similar functions or properties; active ingredients that promote skin repair, such as vitamin C, hyaluronic acid, beta-glucan, ceramides, shea butter and others with similar functions or properties; emollients, such as mineral oil, plant butters (e.g., shea and cocoa), lanolin, petrolatum, paraffin, beeswax, squalene, cetyl alcohol, triethyhexanoin and others with similar functions or properties; vitamins, such as vitamins A, C, E, D, K, B3, B5; and anti-oxidants, such as vitamin C, choline, catechins and others with similar functions or properties. The stored materials may be a combination of one or more disinfectants, fragrances, and/or skin-care ingredients that are slowly released over time.

The shell of the micelles structure is formed of polymers with antimicrobial properties and the ability to release the stored materials over time. Polymers with one or more antimicrobial properties form 0.5 to 95 wt % of the shell material and include, but are not limited to, anionic, cationic and nonionic polymers, where the polymers may contain primary, secondary and tertiary amines, zwitterionics, or quarternary ammoniums. Some examples include, but are not limited to, polyethylenimine (PEI), polyquarternium, polyhexamethylene biguanide (PHMB), poly(diallyldimethylammonium chloride (PDDA), functionalized chitosan (CHI) or similar polymers with bactericidal, virucidal or sporicidal activities. The chemical structure for the exemplary polyethylenimine (PEI) is shown below:

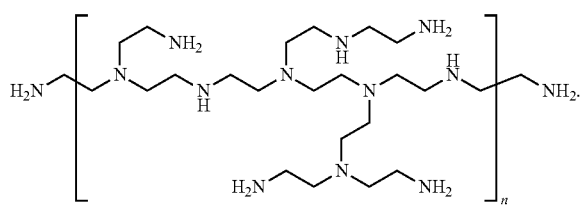

The disinfecting capsules form a micelles structure and a stable colloid that is incorporated in the formulation of water-based hand sanitizers as an antimicrobial ingredient, providing prolonged disinfection and also releasing fragrances and/or skin-care ingredient over time. The formulations for the water-based hand foam sanitizers, as will be described in greater detail below, include the disinfecting capsules, foaming and stabilizing agents and skin-care ingredients, which are suitable for air-foaming. The hand sanitizers may also include the disinfecting capsules, thickeners and viscosity enhancers, and skin-care ingredients, for producing a liquid gel for hand disinfection.

FIG. 1A shows disinfecting capsules made from the exemplary antimicrobial polymer polyethylenimine (PEI), and FIG. 1B shows disinfecting capsules made from the exemplary combination of PEI and polyhexamethylene biguanide (PHMB). FIGS. 1A and 1B are each 500× magnifications. The sizes of the capsules are tunable using surfactants and co-solvents, such as, for example, alcohols. This can be seen in FIGS. 2A, 2B and 2C, with 0 wt %, 0.1 wt % and 0.2 wt % sodium dodecyl sulfate (SDS) as a surfactant, respectively. FIGS. 2A, 2B and 2C are each 200× magnifications. The disinfecting capsules without stored disinfectants are active for disinfection of microorganisms, as shown in FIG. 3. In FIG. 1A, the PEI disinfecting capsules are referred to herein as capsules A1, as will be described in detail with reference to Example 1 below. The combination PEI and PHMB capsules of FIG. 1B are referred to herein as capsules D1, as will be described in greater detail with reference to Example 10 below. Each of the capsules shown in FIGS. 2A, 2B and 2C are referred to herein as capsules D3, as will be described in greater detail in Example 12 below. FIG. 3 compares the bactericidal properties of capsules A1 (Example 1), B1 (Example 4), C1 (Example 7), D1 (Example 10), E1 (Example 13), and F1 (Example 16).

Figure 5:
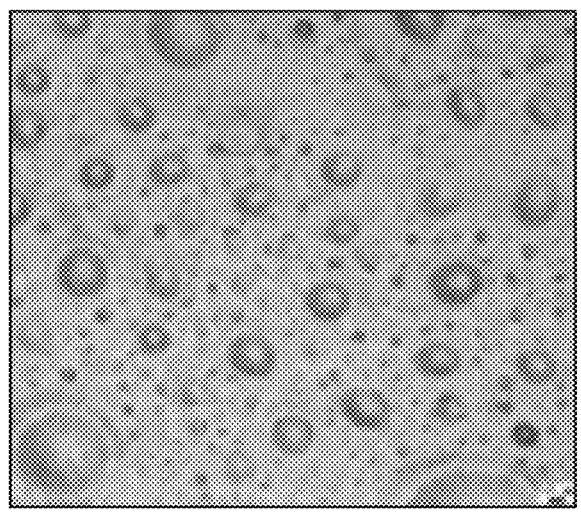
FIG. 5 is a 200× microscope image of a suspension of type A1 disinfecting capsules with farnesol.
Figure 6:
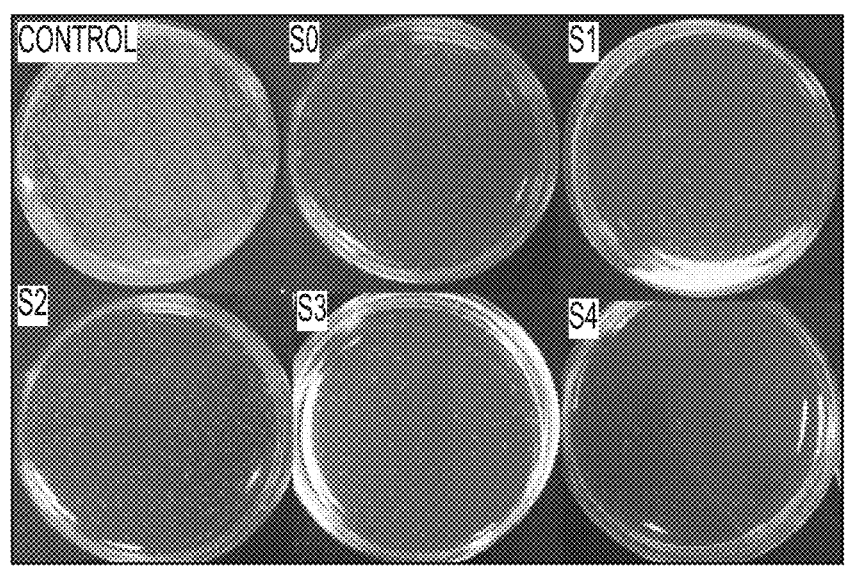
FIG. 6 is an image showing a comparison between a control sample and (S0) type A1 disinfecting capsules, (S1) type A1 disinfecting capsules with 35 ppm farnesol, (S2) type A1 disinfecting capsules with 70 ppm farnesol, (S3) type A1 disinfecting capsules with 350 ppm farnesol, and (S4) type A1 disinfecting capsules with 700 ppm farnesol, each for a contact time of 60 seconds with $10^5$ S. aureus.

FIG. 4 is a 200× magnification showing a suspension of capsules A1 in thyme oil, and FIG. 5 is a 200× magnification showing a suspension of capsules A1 in farnesol. It can be clearly seen that the capsules are larger with the stored disinfectants. FIG. 6 shows the bactericidal properties of the A1-farnesol suspension for contact of 60 seconds with $10^5$ S. aureus, comparing a control sample against empty A1 disinfecting capsules (S0), A1 capsules with 35 ppm farnesol (S1), A1 capsules with 70 ppm farnesol (S2), A1 capsules with 350 ppm farnesol (S3), and A1 capsules with 700 ppm farnesol (S4). FIG. 6 further illustrates the storage capability of the disinfecting capsules and the release of the active content. The S0 sample shows a 90% reduction in viable bacteria, the S1 sample shows a 97% reduction in viable bacteria, the S2 sample shows a 97.5% reduction in viable bacteria, the S3 sample shows a 98.8% reduction in viable bacteria, and the S4 sample shows a 99.25% reduction in viable bacteria.

The formulation of Example 38 (formulation 1) below is an active sanitizer and, when applied, achieved better than 99% decrease in viable E. coli ($10^5$ CFU) within 60 seconds of contact. The formulation contained disinfecting capsules A1. A colorant can be added to the hand sanitizer to produce foams of different colors. Disinfecting capsules containing thyme oil are also stable and can produce stable foam.

Figure 7A:
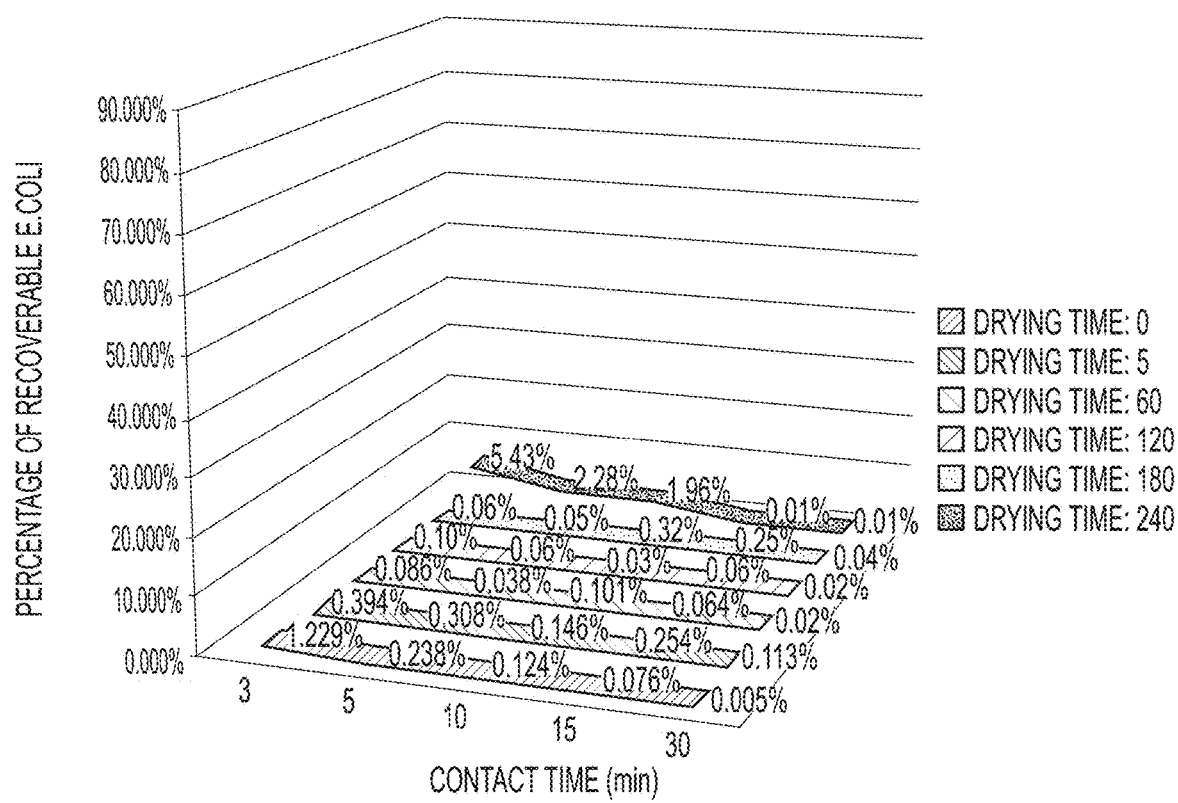
FIG. 7A is a graph showing the bactericidal activity of a hand foam sanitizer (formulation 2) as a function of contact time for samples applied for 5, 60, 120, 180 and 240 minutes before testing against $10^5$ CFU E. coli.
Figure 7B:
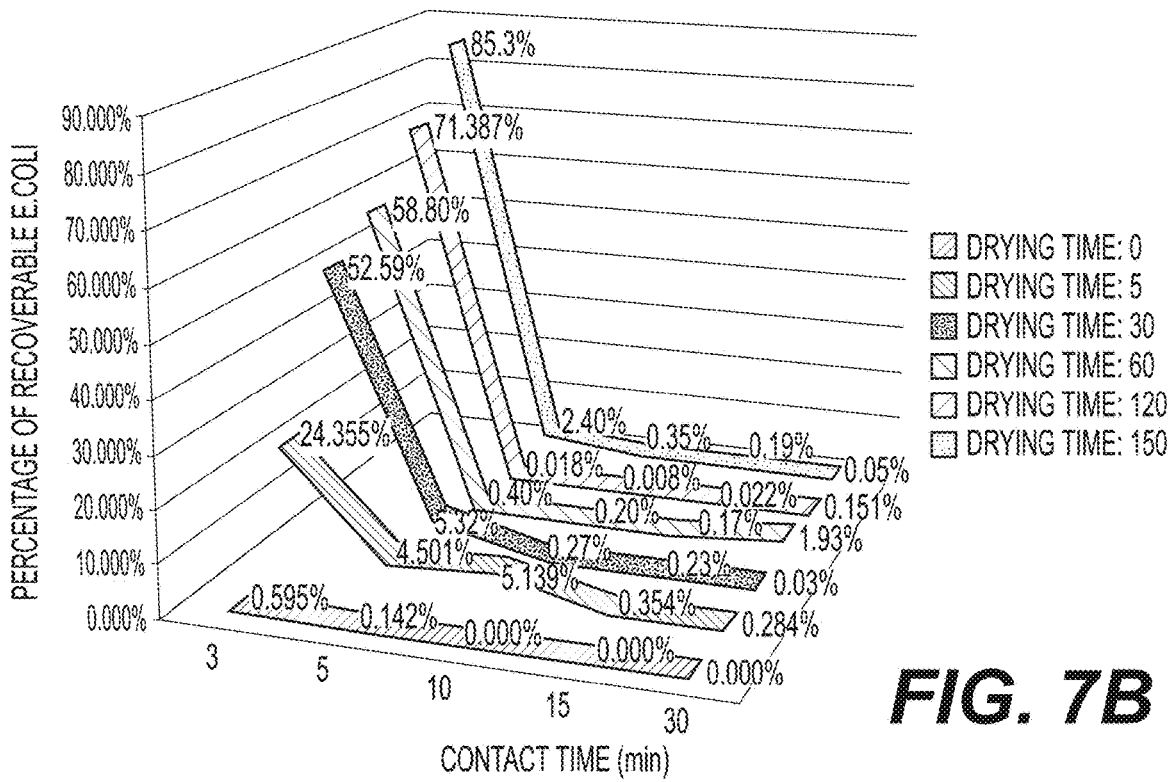
FIG. 7B is a graph showing the bactericidal activity of a conventional alcohol-based hand sanitizer as a function of contact time for samples applied for 5, 60, 120, 180 and 240 minutes before testing against $10^5$ CFU E. coli.
Figure 8:
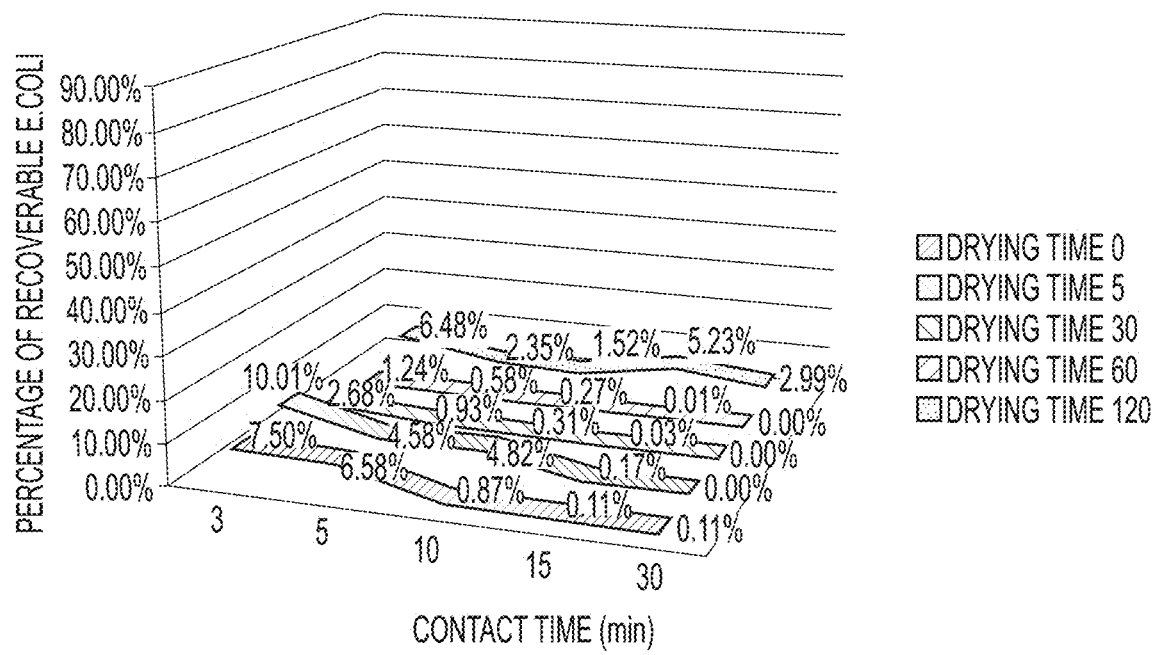
FIG. 8 is a graph showing the bactericidal activity of a hand foam sanitizer (formulation 10) as a function of contact time for samples applied for 5, 60, 120, 180 and 240 minutes before testing against $10^5$ CFU E. coli.
Figure 9:
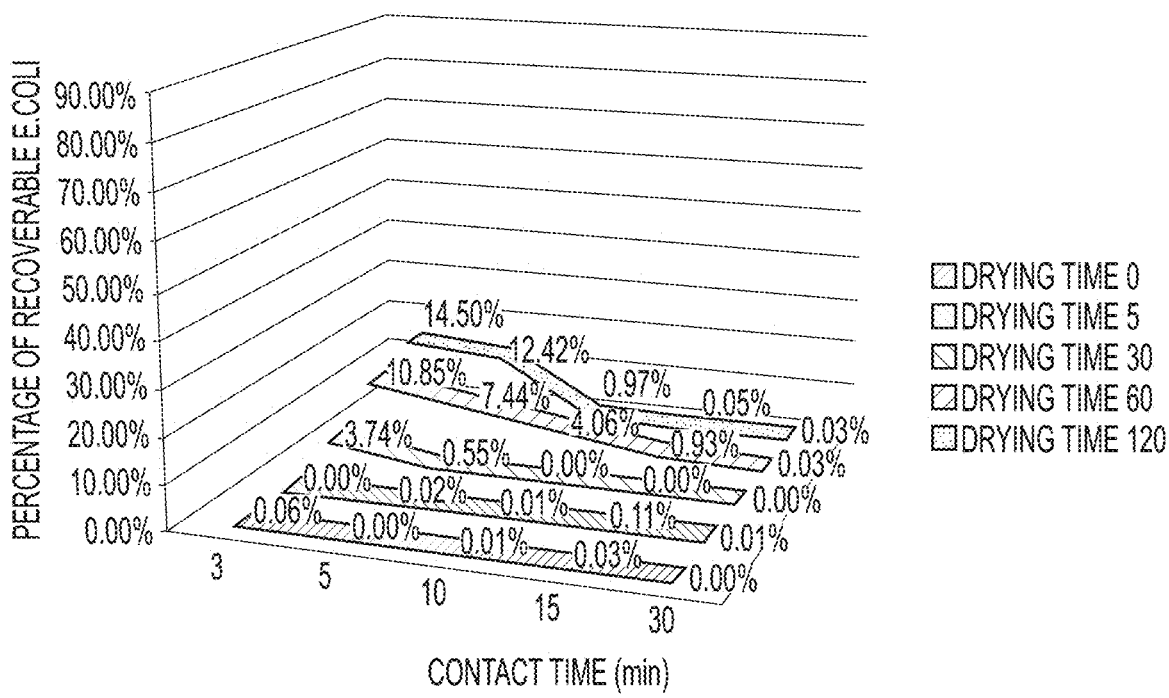
FIG. 9 is a graph showing the bactericidal activity of a hand foam sanitizer (formulation 11) as a function of contact time for samples applied for 5, 60, 120, 180 and 240 minutes before testing against $10^5$ CFU E. coli.

Hand disinfection was performed according to the following procedure: The hands were sanitized with 75% vol. of ethanol for 15 seconds, rinsed with tap water for 20 seconds, and dried with two pieces of clean paper towel, followed by 1 minute of air drying. The fingertips on the left hand were sampled. Afterward, 1 milliliter of foam was applied and spread evenly over the hand and dried by rubbing the hands together. A suspension containing ten microliters of E. coli ($10^6$ CFU) was evenly spread over a 1 cm$^2$ area of each fingertip. The fingertips were then sampled, one after the other, following 3, 5, 10, 15 and 30 minutes of bacterial challenge. The sampling was done by gently pressing the fingers onto agar and rolling it for 5 seconds. The recovered viable E. coli was then counted. The experiment was carried out in triplicate. This was followed by a series of experiment where the bacteria was challenged on the fingertips after 5, 60, 120, 180 and 240 minutes of using the sanitizers. FIGS. 7A, 7B, 8 and 9 show that the hand foam sanitizers have persistent disinfection properties and can keep the hands clean from microbial contamination up to 4 hours after usage. It can be seen that the recoverable E. coli was less than 1.2% on hands disinfected with the hand foam sanitizers. FIG. 7A shows the bactericidal activity of a hand foam sanitizer made from formulation 2 of Example 39 below as a function of contact time for samples applied over 5, 60, 120, 180 and 240 minutes before the test. FIG. 7B is a comparison using the same parameters for a conventional alcohol-based hand sanitizer. For each of FIGS. 7A and 7B, the measured bactericidal activity was against $10^5$ CFU E. coli. FIG. 8 shows the bactericidal activity of a hand foam sanitizer made from formulation 10 of Example 47 below as a function of contact time for samples applied over 5, 60, 120, 180 and 240 minutes before the test. The measured bactericidal activity was against $10^5$ CFU E. coli. FIG. 9 shows the bactericidal activity of a hand foam sanitizer made from formulation 11 of Example 48 below as a function of contact time for samples applied over 5, 60, 120, 180 and 240 minutes before the test. The measured bactericidal activity was against $10^5$ CFU E. coli.

Figure 10:
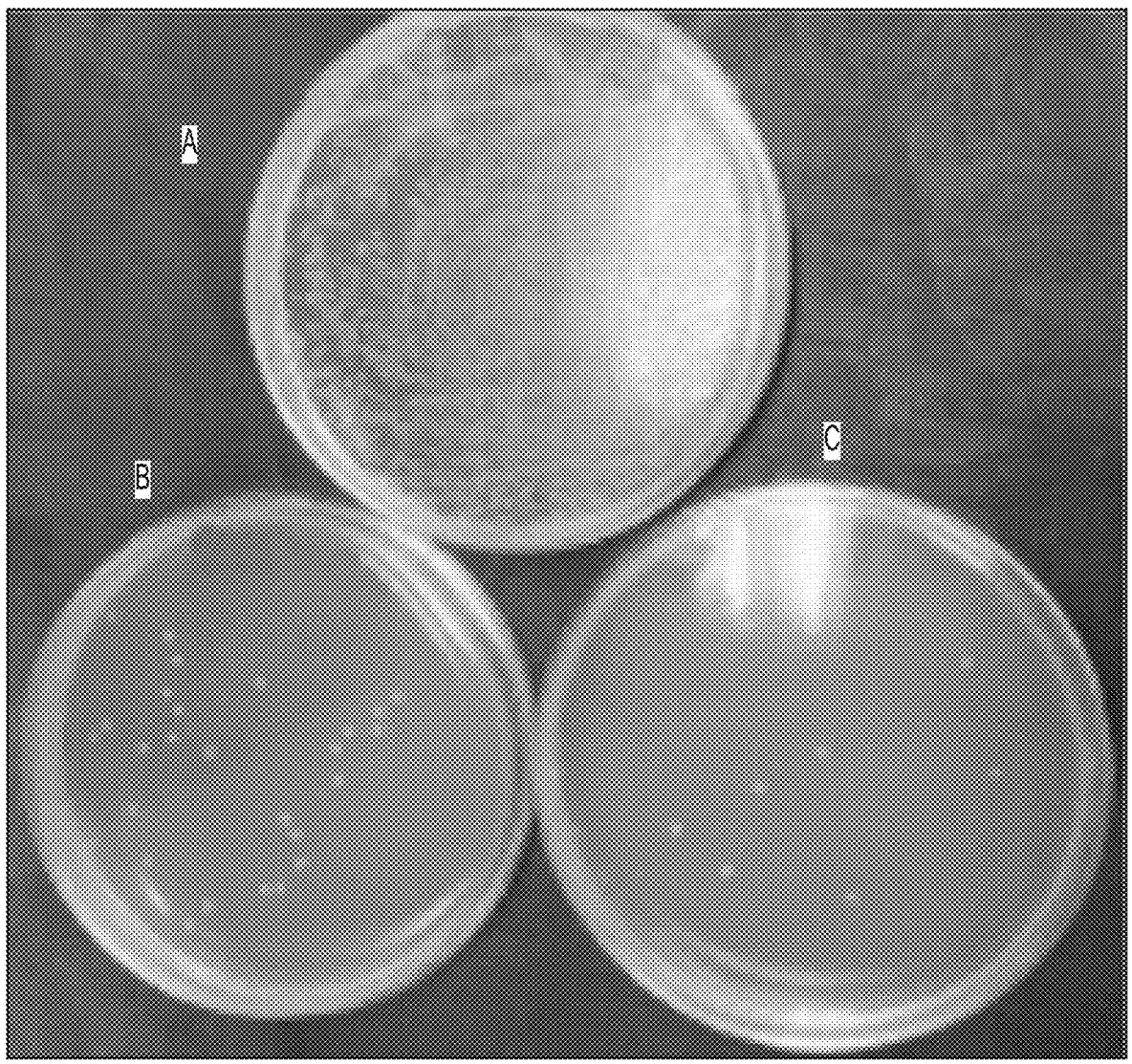
FIG. 10 shows a comparison of bactericidal activity between (a) a control sample, (b) a hand gel sanitizer (formulation 8) with a contact time of 30 seconds against $10^5$ CFU E. coli, and (c) the hand gel sanitizer (formulation 8) with a contact time of 60 seconds against $10^5$ CFU E. coli.

FIG. 10 shows that a hand gel sanitizer using the disinfecting capsules also possessed similarly high bactericidal activities, even at a very short contact time of 30 seconds. In FIG. 10, the "a" sample represents a control, the "b" sample shows contact of 30 seconds using a hand gel sanitizer with formulation 8 of Example 45 below, and the "c" sample shows contact of 60 seconds using the hand gel sanitizer with formulation 8 of Example 45 below. The measured bactericidal activity is >99% against $10^5$ CFU E. coli.

As a further alternative, a hand foam sanitizer may be prepared by providing a skin care ingredient-containing solution separately from a suspension containing the at least one foaming agent and the volume of disinfecting capsules suspended therein. The skin care ingredient-containing solution can then be selectively mixed with the suspension at a desired ratio. It should be understood that the skin care ingredient(s) and foaming agent(s) may be any desired skin care ingredient(s) and foaming agent(s), such as those described with regard to the previous embodiments.

Example 1

Preparation of Disinfecting Capsules A1

A solution of 0.1-40 wt % polyethylenimine and 0.1 to 10 wt % polyvinyl alcohol was dissolved in sterile distilled water and mixed under strong agitation to produce a colloidal suspension, which was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer, such as poly(ethylene glycol) methacrylate or poly(ethylene glycol) methyl ether methacrylate of molecular weight of 500-1000 g/mol.

Example 2

Preparation of Disinfecting Capsules A2

A solution of 0.1-40 wt % polyethylenimine and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures. Also, if needed, the polymer can be cross-linked with a third polymer, such as poly(ethylene glycol) methacrylate or poly(ethylene glycol) methyl ether methacrylate of molecular weight of 500-1000 g/mol.

Example 3

Preparation of Disinfecting Capsules A3

A solution of 0.1-40 wt % polyethylenimine and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 4

Preparation of Disinfecting Capsules B1

A solution of 0.1-30 wt % polyhexamethylene biguanide and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures.

Example 5

Preparation of Disinfecting Capsules B2

A solution of 0.1-30 wt % polyhexamethylene biguanide and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures.

Example 6

Preparation of Disinfecting Capsules B3

A solution of 0.1-30 wt % polyhexamethylene biguanide and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures.

Example 7

Preparation of Disinfecting Capsules C1

A solution of 0.1-40 wt % poly diallyldimethylammonium chloride and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures.

Example 8

Preparation of Disinfecting Capsules C2

A solution of 0.1-40 wt % poly diallyldimethylammonium chloride and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures.

Example 9

Preparation of Disinfecting Capsules C3

A solution of 0.1-40 wt % poly diallyldimethylammonium chloride and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures.

Example 10

Preparation of Disinfecting Capsules D1

A solution of 0.1-40 wt % polyethylenimine, 0.01 to 5 wt % polyhexamethylene biguanide, and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer, such as poly(ethylene glycol) methacrylate or poly(ethylene glycol) methyl ether methacrylate of molecular weight of 500-1000 g/mol.

Example 11

Preparation of Disinfecting Capsules D2

A solution of 0.1-40 wt % polyethylenimine, 0.01 to 5 wt % polyhexamethylene biguanide, and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures. Also, if needed, the polymer can be cross-linked with a third polymer, such as poly(ethylene glycol) methacrylate or poly(ethylene glycol) methyl ether methacrylate of molecular weight of 500-1000 g/mol.

Example 12

Preparation of Disinfecting Capsules D3

A solution of 0.1-40 wt % polyethylenimine, 0.01 to 5 wt % polyhexamethylene biguanide, and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer, such as poly(ethylene glycol) methacrylate or poly(ethylene glycol) methyl ether methacrylate of molecular weight of 500-1000 g/mol.

Example 13

Preparation of Disinfecting Capsules E1

A solution of 0.1-40 wt % polyethylenimine, 0.01 to 20 wt % poly diallyldimethylammonium chloride, and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 14

Preparation of Disinfecting Capsules E2

A solution of 0.1-40 wt % polyethylenimine, 0.01 to 20 wt % poly diallyldimethylammonium chloride, and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 15

Preparation of Disinfecting Capsules E3

A solution of 0.1-40 wt % polyethylenimine, 0.01 to 20 wt % poly diallyldimethylammonium chloride, and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 16

Preparation of Disinfecting Capsules F1

A solution of 0.1-40 wt % polyethylenimine, 0.01 to 20 wt % poly diallyldimethylammonium chloride, 0.01 to 5 wt % polyhexamethylene biguanide, and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 17

Preparation of Disinfecting Capsules F2

A solution of 0.1-40 wt % polyethylenimine, 0.01 to 20 wt % poly diallyldimethylammonium chloride, 0.01 to 5 wt % polyhexamethylene biguanide, and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 18

Preparation of Disinfecting Capsules F3

A solution of 0.1-40 wt % polyethylenimine, 0.01 to 20 wt % poly diallyldimethylammonium chloride, 0.01 to 5 wt % polyhexamethylene biguanide, and 0.1 to 10 wt % polyvinylpyrrolidone was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures. Also, if needed, the polymer can be cross-linked with a third polymer such as poly(ethylene glycol) methacrylate or poly(ethylene glycol) methyl ether methacrylate of molecular weight of 500-1000 g/mol.

Example 19

Preparation of Disinfecting Capsules G1

A solution of 0.1-40 wt % chitosan or functionalized chitosan of molecular weight of 5000 to 120000 g/mole and 0.1 to 10 wt % polyvinyl alcohol was dissolved in sterile distilled water and mixed under strong agitation to produce a colloidal suspension that was generally transparent to translucent in appearance. A small amount of surfactants, such as sodium dodecyl sulfate and/or ammonium lauryl sulfate, were added to control the size and shape of the micelle structures.

Example 20

Preparation of Disinfecting Capsules G2

A solution of 0.1-40 wt % chitosan or functionalized chitosan of molecular weight of 5000 to 120000 g/mole and 0.1 to 10 wt % Pluronic P123 or Pluronic F127 was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures.

Example 21

Preparation of Disinfecting Capsules G3

A solution of 0.1-40 wt % chitosan or functionalized chitosan of molecular weight of 5000 to 120000 g/mole and 0.1 to 10 wt % polyvinylpyrrolidone was dissolved in sterile distilled water and mixed under strong agitation to produce a colloidal suspension that was generally translucent in appearance. A small amount of surfactants, such as sodium dodecyl sulfate and/or ammonium lauryl sulfate, were added to control the size and shape of the micelle structures.

Example 22

Preparation of Disinfecting Capsule H1

A solution of 0.1 to 40 wt % polyquarterniums including, but not limited to, hydroxyethylcellulose ethoxylate quarternized, and poly[(2-ethyldimethyl-ammonioethyl chloride)-co-(1-vinylpyrrolidone] of molecular weights ranging from 5000 to 1000000 g/mol was dissolved in sterile distilled water, and then added to a 0.1 to 10 wt % polyvinyl alcohol solution in volume ratios from 5:1 to 1:5. A colloidal suspension that was generally transparent to translucent in appearance was produced, following mixing under strong agitation.

Example 23

Preparation of Disinfecting Capsule H2

A solution of 0.1 to 40 wt % polyquarterniums including, but not limited to hydroxyethylcellulose ethoxylate quarternized, and poly[(2-ethyldimethyl-ammonioethyl chloride)-co-(1-vinylpyrrolidone] of molecular weights ranging from 5000 to 1000000 g/mol was dissolved in sterile distilled water, and then added to a 0.1 to 10 wt % Pluronic P123 or Pluronic F127 solution in volume ratios from 5:1 to 1:5. A colloidal suspension that was generally transparent to translucent in appearance was produced, following mixing under strong agitation.

Example 24

Preparation of Disinfecting Capsule H3

A solution of 0.1 to 40 wt % polyquarterniums including, but not limited to, hydroxyethylcellulose ethoxylate quarternized, and poly[(2-ethyldimethyl-ammonioethyl chloride)-co-(1-vinylpyrrolidone] of molecular weights ranging from 5000 to 1000000 g/mol was dissolved in sterile distilled water, and then added to a 0.1 to 10 wt % polyvinylpyrrolidone in volume ratios from 5:1 to 1:5. A colloidal suspension that was generally transparent to translucent in appearance was produced, following mixing under strong agitation.

Example 25

Preparation of Disinfecting Capsules A1-Thyme Oil

Polyethylenimine with a molecular weight of 1200 to 10000 g/mol was dissolved in sterile distilled water to prepare a polymer solution with concentrations of 1 to 20 wt %. A measured amount of thyme oil was added to 0.1 to 10 wt % polyvinyl alcohol solution and emulsified. The polymer solution and the emulsion containing thyme oil were mixed in volume ratios from 5:1 to 1:5, followed by rapid mixing and ultrasonication (ca 1 min) to produce disinfecting capsules. Tween® 80, a polysorbate surfactant, was added to stabilize the colloid.

Example 26

Preparation of Disinfecting Capsules A1-Farnesol

Polyethylenimine with a molecular weight of 1200 to 10000 g/mol was dissolved in sterile distilled water to prepare a polymer solution with concentrations of 1 to 20 wt %. A measured amount of farnesol dissolved in dimethyl sulfoxide (DMSO)/water solution to give a final concentration in the range of 10 wt % to 50 wt % was added to 0.1 to 10 wt % polyvinyl alcohol solution and emulsified. The polymer solution and the emulsion containing farnesol were mixed in volume ratios from 5:1 to 1:5, followed by rapid mixing and ultrasonication (ca 1 min) to produce disinfecting capsules. Tween® 80 was added to stabilize the colloid.

Example 27

Preparation of Disinfecting Capsules A1-Thyme Oil and Citrus Oil

Polyethylenimine with a molecular weight of 1200 to 10000 g/mol was dissolved in sterile distilled water to prepare a polymer solution with concentrations of 1 to 20 wt %. A measured amount of thyme oil mixed with citrus oil was added to 0.1 to 10 wt % polyvinyl alcohol solution and emulsified. The polymer solution and the emulsion containing essential oils were mixed in volume ratios from 5:1 to 1:5, followed by rapid mixing and ultrasonication (ca 1 min) to produce disinfecting capsules. Tween® 80 was added to stabilize the colloid.

Example 28

Preparation of Disinfecting Capsules A1-Thyme Oil and Lavender Oil

Polyethylenimine with a molecular weight of 1200 to 10000 g/mol was dissolved in sterile distilled water to prepare a polymer solution with concentrations of 1 to 20 wt %. A measured amount of thyme oil mixed with lavender oil was added to 0.1 to 10 wt % polyvinyl alcohol solution and emulsified. The polymer solution and the emulsion containing essential oils were mixed in volume ratios from 5:1 to 1:5, followed by rapid mixing and ultrasonication (ca 1 min) to produce disinfecting capsules. Tween® 80 was added to stabilize the colloid.

Example 29

Preparation of Disinfecting Capsules A1-Thyme Oil, Citrus Oil and Vitamin E

Polyethylenimine with a molecular weight of 1200 to 10000 g/mol was dissolved in sterile distilled water to prepare a polymer solution with concentrations of 1 to 20 wt %. A measured amount of a mixture of thyme oil, citrus oil and vitamin E was added to 0.1 to 10 wt % polyvinyl alcohol solution and emulsified. The polymer solution and the emulsion containing the disinfectant, fragrance and skin-care ingredients were mixed in volume ratios from 5:1 to 1:5, followed by rapid mixing and ultrasonication (ca 1 min) to produce disinfecting capsules. Tween® 80 was added to stabilize the colloid.

Example 30

Preparation of Disinfecting Capsules A1-Thymol

Polyethylenimine with a molecular weight of 1200 to 10000 g/mol was dissolved in sterile distilled water to prepare a polymer solution with concentrations of 1 to 20 wt %. A measured amount of 80 wt % thymol dissolved in dipropylene glycol (DPG) was added to 0.1 to 10 wt % polyvinyl alcohol solution and emulsified. The polymer solution and the emulsion containing the disinfectant, fragrance and skin-care ingredients were mixed in volume ratios from 5:1 to 1:5, followed by rapid mixing and ultrasonication (ca 1 min) to produce disinfecting capsules. Tween® 80 was added to stabilize the colloid.

Example 31

Preparation of Disinfecting Capsules A1-Isopropanol

Polyethylenimine with a molecular weight of 1200 to 10000 g/mol was dissolved in sterile distilled water to prepare a polymer solution with concentrations of 1 to 20 wt %. A measured amount of isopropanol was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 32

Preparation of Disinfecting Capsules A1-Chlorhexidine

Polyethylenimine with a molecular weight of 1200 to 10000 g/mol was dissolved in sterile distilled water to prepare a polymer solution with concentrations of 1 to 20 wt %. A measured amount of chlorhexidine was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 33

Preparation of Disinfecting Capsules A3-Thyme Oil

Polyethylenimine with a molecular weight of 1200 to 10000 g/mol was dissolved in sterile distilled water to prepare a polymer solution with concentrations of 1 to 20 wt %. A measured amount of thyme oil was added to 0.1 to 10 wt % polyvinyl pyrrolidone solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 34

Preparation of Disinfecting Capsules D1-Thyme Oil

A solution of 0.1-40 wt % polyethylenimine and 0.01 to 5 wt % polyhexamethylene biguanide was dissolved in sterile distilled water. A measured amount of thyme oil was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 35

Preparation of Disinfecting Capsules E1-Thyme Oil

A solution of 0.1-40 wt % polyethylenimine and 0.01 to 20 wt % poly diallyldimethylammonium chloride was dissolved in sterile distilled water. A measured amount of thyme oil was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 36

Preparation of Disinfecting Capsules F1-Thyme Oil

A solution of 0.1-40 wt % polyethylenimine, 0.01 to 5 wt % polyhexamethylene biguanide and 0.01 to 20 wt % poly diallyldimethylammonium chloride was dissolved in sterile distilled water. A measure amount of thyme oil was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 37

Preparation of Disinfecting Capsules G1-Thyme Oil

A solution of 0.1-40 wt % chitosan or functionalized chitosan of molecular weight of 5000 to 120000 g/mole and 0.1 to 10 wt % polyvinyl alcohol was dissolved in sterile distilled water. A measured amount of thyme oil was added to 0.1 to 10 wt % polyvinyl alcohol solution and emulsified. The polymer solution and the emulsion were mixed in volume ratios from 5:1 to 1:5, followed by rapid mixing and ultrasonication (ca 1 min) to produce disinfecting capsules. Tween® 80 was added to stabilize the colloid.

Example 38

Hand Foam Sanitizer Formulation 1

Table 1 below is a composition of a hand foam sanitizer formed from A1 disinfecting capsules, and was prepared by mixing the listed components in sequence to obtain a water-based colloidal suspension.

TABLE 1

Hand Foam Sanitizer Formulation 1

| Component | Ingredient | Weight Percent |
| --- | --- | --- |
| Antimicrobial Polymer | Polyethylenimine | 0.7 |
| Stabilizer | Polyvinyl alcohol | 0.35 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Hand Foam Sanitizer Formulation 1A

Table 2 below shows the composition of a hand foam sanitizer formed from A1 disinfecting capsules, and was prepared by mixing the listed components in sequence to obtain a water-based colloidal suspension. Colorant can be added in form of colored dye or pigment.

TABLE 2

Hand Foam Sanitizer Formulation 1A

| Component | Ingredient | Weight Percent |
| --- | --- | --- |
| Antimicrobial Polymer | Polyethylenimine | 0.7 |
| Stabilizer | Polyvinyl alcohol | 0.35 |
| Foam Stabilizer | Tween 80 ® | 2.5 |
| Foamer | Sodium dodecyl sulfate | 2.5 |
| Moisturing and Wound Healing | Vitamin E | ≤0.02 |

TABLE 2-continued

Hand Foam Sanitizer Formulation 1A

| Component | Ingredient | Weight Percent |
| --- | --- | --- |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 39

Hand Foam Sanitizer Formulation 2

Table 3 below shows a composition of a hand foam sanitizer formed from A1-thyme oil disinfecting capsules, and was prepared by mixing the listed components in sequence to obtain a water-based colloidal suspension. Disinfection remains active after 4 hours from application when compared to alcohol.

TABLE 3

Hand Foam Sanitizer Formulation 2

| Component | Ingredient | Weight Percent |
| --- | --- | --- |
| Antimicrobial Polymer | Polyethylenimine | 0.7 |
| Stabilizer | Polyvinyl alcohol | 0.35 |
| Disinfectant | Thyme oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 40

Hand Foam Sanitizer Formulation 3

Table 4 below shows a composition of a hand foam sanitizer formed from A1-thyme oil disinfecting capsules with citrus oil fragrance, and was prepared by mixing the listed components in sequence to obtain a water-based colloidal suspension.

TABLE 4

Hand Foam Sanitizer Formulation 3

| Component | Ingredient | Weight Percent |
| --- | --- | --- |
| Antimicrobial Polymer | Polyethylenimine | 0.7 |
| Stabilizer | Polyvinyl alcohol | 0.35 |
| Disinfectant | Thyme oil | 0.03 |
| Fragrance | Citrus oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |

TABLE 4-continued

Hand Foam Sanitizer Formulation 3

| Component | Ingredient | Weight Percent |
|---|---|---|
| | Critic Acid (pH adjustment to PH = 5.5 to 6.5) | ≤0.02 |
| | Water | Balance to 100% |

Example 41

Hand Foam Sanitizer Formulation 4

Table 5 below shows a composition of a hand foam sanitizer formed from A1-thyme oil disinfecting capsules with lavender fragrance, and was prepared by mixing the listed components in sequence to obtain a water-based colloidal suspension.

TABLE 5

Hand Foam Sanitizer Formulation 4

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Fragrance | Lavender oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 42

Hand Foam Sanitizer Formulation 5

Table 6 below shows a composition of a hand foam sanitizer formed from A1-thyme oil disinfecting capsules with lavender fragrance and vitamin E moisturizer, and was prepared by mixing the listed components in sequence to obtain a water-based colloidal suspension.

TABLE 6

Hand Foam Sanitizer Formulation 5

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Fragrance | Lavender oil | 0.03 |
| Moisturizer | Vitamin E | 0.02 |
| Foam Stabilizer | Tween ® 80 | 2.5 |
| Foamer | Sodium dodecyl sulfate | 2.5 |
| Moisturing and Wound Healing | Sodium hyaluronic | ≤0.02 |
| Freshness Handfeel | Frescolat ® MGA (Menthone Glycerin Acetal) | ≤0.02 |

TABLE 6-continued

Hand Foam Sanitizer Formulation 5

| Component | Ingredient | Weight Percent |
|---|---|---|
| | Critic Acid (pH adjustment to PH = 5.5 to 6.5) | ≤0.02 |
| | Water | Balance to 100% |

Example 43

Hand Foam Sanitizer Formulation 6

Table 7 below shows a composition of a hand foam sanitizer formed from A1-thyme oil disinfecting capsules with lavender oil fragrance, and was prepared by mixing the listed components in sequence to obtain a water-based colloidal suspension.

TABLE 7

Hand Foam Sanitizer Formulation 6

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Fragrance | Lavender oil | 0.03 |
| Foam Stabilizer | Tween ® 80 | 2.5 |
| Foamer | Sodium dodecyl sulfate | 2.5 |
| Moisturing and Wound Healing | Sodium hyaluronic Vitamin E | ≤0.02 |
| Emollient | Cetyl alcohol | ≤0.02 |
| Vitamin and Antioxidant | Vitamin C | ≤0.02 |
| Freshness Handfeel | Frescolat ® MGA (Menthone Glycerin Acetal) | ≤0.02 |
| | Critic Acid (pH adjustment to PH = 5.5 to 6.5) | Optional |
| | Water | Balance to 100% |

Example 44

Hand Foam Sanitizer Formulation 7

Table 8 below shows a composition of a hand foam sanitizer formed from B1-thyme oil disinfecting capsules, and was prepared by mixing the listed components in sequence to obtain a water-based colloidal suspension.

TABLE 8

Hand Foam Sanitizer Formulation 7

| Component | Ingredient | Weight Percent |
|---|---|---|
| Antimicrobial Polymer | Polyhexamethylene biguanide | 0.2 |
| Stabilizer | Polyvinyl alcohol | 0.35 |
| Disinfectant | Thyme oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 45

Hand Foam Sanitizer Formulation 8

Table 9 below shows a composition of a hand foam sanitizer formed from D1-thyme oil disinfecting capsules with lavender oil fragrance, and was prepared by mixing the listed components in sequence to obtain a water-based colloidal suspension.

TABLE 9

Hand Foam Sanitizer Formulation 8

| Component | Ingredient | Weight Percent |
| --- | --- | --- |
| Antimicrobial Polymer | Polyethylenimine | 0.7 |
| | Polyhexamethylene biguanide | 0.1 |
| Stabilizer | Polyvinyl alcohol | 0.35 |
| Disinfectant | Thyme oil | 0.03 |
| Fragrance | Lavender oil | 0.03 |
| Foam Stabilizer | Tween ® 80 | 2.5 |
| Foamer | Sodium dodecyl sulfate | 2.5 |
| Moisturing and Wound Healing | Sodium hyaluronic Vitamin E | ≤0.02 |
| Emollient | Cetyl alcohol | ≤0.02 |
| Vitamin and Antioxidant | Vitamin C | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 46

Hand Foam Sanitizer Formulation 9

Table 10 below shows a composition of a hand foam sanitizer formed from D1-thyme oil disinfecting capsules with lavender oil fragrance, and was prepared by mixing the listed components in sequence to obtain a water-based colloidal suspension.

TABLE 10

Hand Foam Sanitizer Formulation 9

| Component | Ingredient | Weight Percent |
| --- | --- | --- |
| Antimicrobial Polymer | Polyethylenimine | 0.7 |
| | Polyhexamethylene biguanide | 0.1 |
| Stabilizer | Polyvinyl alcohol | 0.35 |
| Disinfectant | Thyme oil | 0.03 |
| Fragrance | Lavender oil | 0.03 |
| Skin-care | Vitamin E | 0.02 |
| Foam Stabilizer | Tween ® 80 | 2.5 |
| Foamer | Sodium dodecyl sulfate | 2.5 |
| Moisturing and Wound Healing | Sodium hyaluronic | ≤0.02 |
| Emollient | Cetyl alcohol | ≤0.02 |
| Vitamin and Antioxidant | Vitamin C | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 47

Hand Foam Sanitizer Formulation 10

Table 11 below shows a composition of a hand foam sanitizer formed from A1-gerariol oil disinfecting capsules, and was prepared by mixing the listed components in sequence to obtain a water-based colloidal suspension.

TABLE 11

Hand Foam Sanitizer Formulation 10

| Component | Ingredient | Weight Percent |
| --- | --- | --- |
| Antimicrobial Polymer | Polyethylenimine | 0.7 |
| Stabilizer | Polyvinyl alcohol | 0.35 |
| Disinfectant | Gerariol oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 48

Hand Foam Sanitizer Formulation 11

Table 12 below shows a composition of a hand foam sanitizer formed from A1-origanum oil disinfecting capsules, and was prepared by mixing the listed components in sequence to obtain a water-based colloidal suspension.

TABLE 12

Hand Foam Sanitizer Formulation 11

| Component | Ingredient | Weight Percent |
| --- | --- | --- |
| Antimicrobial Polymer | Polyethylenimine | 0.7 |
| Stabilizer | Polyvinyl alcohol | 0.35 |
| Disinfectant | Origarum oil | 0.03 |
| Foam Stabilizer | Tween ® 80 | 2.5 |
| Foamer | Sodium dodecyl sulfate | 2.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 49

Hand Gel Sanitizer Formulation 1

Table 13 below shows a composition of a hand gel sanitizer formed from A1 disinfecting capsules, and was prepared by mixing the listed components in sequence to obtain a water-based colloidal suspension.

Example 50

Hand Gel Sanitizer Formulation 1

Table 13 below shows a composition of a hand gel sanitizer Formulation 1.

TABLE 13

Hand Gel Sanitizer Formulation 1

| Component | Ingredient | Weight Percent |
|---|---|---|
| Antimicrobial Polymer | Polyethylenimine | 0.7 |
| Stabilizer | Polyvinyl alcohol | 0.35 |
| Thickener and Viscosity Enhancer | Polyethylene Glycol | 0.01-0.1 |
|  | Guar gum | 0.01-0.1 |
| Moisturing and Wound Healing | Vitamin E | ≤0.02 |
| Freshness Handfeel | Frescolat ® MGA (Menthone Glycerin Acetal) | ≤0.02 |
|  | Critic Acid (pH adjustment to PH = 5.5 to 6.5) | ≤0.02 |
|  | Water | Balance to 100% |

Example 50

Hand Gel Sanitizer Formulation 2

Table 14 below shows a composition of a hand gel sanitizer formed from A1 disinfecting capsules and was prepared by mixing the listed components in sequence to obtain a water-based colloidal suspension.

TABLE 14

Hand Gel Sanitizer Formulation 2

| Component | Ingredient | Weight Percent |
|---|---|---|
| Antimicrobial Polymer | Polyethylenimine | 0.7 |
|  | Polyhexamethylene biguanide | 0.1 |
| Stabilizer | Polyvinyl alcohol | 0.35 |
| Thickener and Viscosity Enhancer | Polyethylene Glycol | 0.01-0.1 |
|  | Guar gum | 0.01-0.1 |
| Moisturing and Wound Healing | Vitamin E | ≤0.02 |
| Freshness Handfeel | Frescolat ® MGA (Menthone Glycerin Acetal) | ≤0.02 |
|  | Critic Acid (pH adjustment to PH = 5.5 to 6.5) | ≤0.02 |
|  | Water | Balance to 100% |

Example 51

Hand Gel Sanitizer Formulation 3

Table 15 below shows a composition of a hand gel sanitizer formed from A1-thyme oil disinfecting capsules, and was prepared by mixing the listed components in sequence to obtain a water-based colloidal suspension.

TABLE 15

Hand Gel Sanitizer Formulation 3

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Thickener and Viscosity Enhancer | Polyethylene Glycol | 0.01-0.1 |
|  | Guar gum | 0.01-0.1 |
| Moisturing and Wound Healing | Vitamin E | ≤0.02 |
| Freshness Handfeel | Frescolat ® MGA (Menthone Glycerin Acetal) | ≤0.02 |
|  | Critic Acid (pH adjustment to PH = 5.5 to 6.5) | ≤0.02 |
|  | Water | Balance to 100% |

Example 52

Hand Gel Sanitizer Formulation 4

Table 16 below shows a composition of a hand gel sanitizer formed from A1-thyme oil disinfecting capsules with lavender oil fragrance and was prepared by mixing the listed components in sequence to obtain a water-based colloidal suspension.

TABLE 16

Hand Gel Sanitizer Formulation 4

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Fragrance | Lavender oil | 0.03 |
| Thickener and Viscosity Enhancer | Polyethylene Glycol | 0.01-0.1 |
|  | Guar gum | 0.01-0.1 |
| Fragrance | Lavender oil | 0.5 |
| Moisturing and Wound Healing | Vitamin E | ≤0.02 |
| Freshness Handfeel | Frescolat ® MGA (Menthone Glycerin Acetal) | ≤0.02 |
|  | Critic Acid (pH adjustment to PH = 5.5 to 6.5) | ≤0.02 |
|  | Water | Balance to 100% |

Example 53

Hand Gel Sanitizer Formulation 5

Table 17 below shows a composition of a hand gel sanitizer formed from A1-thyme oil disinfecting capsules with lavender oil fragrance and vitamin E, and was prepared by mixing the listed components in sequence to obtain a water-based colloidal suspension.

TABLE 17

Hand Gel Sanitizer Formulation 5

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Thyme oil | 0.03 |
| Fragrance | Lavender oil | 0.03 |
| Skin-care | Vitamin E | 0.02 |
| Thickener and Viscosity Enhancer | Polyethylene Glycol | 0.01-0.1 |
|  | Guar gum | 0.01-0.1 |
| Fragrance | Lavender oil | 0.5 |
| Moisturing and Wound Healing | Vitamin E | ≤0.02 |
| Freshness Handfeel | Frescolat ® MGA (Menthone Glycerin Acetal) | ≤0.02 |

TABLE 17-continued

Hand Gel Sanitizer Formulation 5

| Component | Ingredient | Weight Percent |
|---|---|---|
| | Critic Acid (pH adjustment to PH = 5.5 to 6.5) | ≤0.02 |
| | Water | Balance to 100% |

Example 54

Hand Gel Sanitizer Formulation 6

Table 18 below shows a composition of a hand gel sanitizer comprising of A1-tea tree oil disinfecting capsules with lavender oil fragrance and eucalyptus oil, and was prepared by mixing the listed components in sequence to obtain a water-based colloidal suspension.

TABLE 18

Hand Gel Sanitizer Formulation 6

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Tea tree oil | 0.03 |
| Fragrance | Lavender oil | 0.03 |
| Skin-care | *Eucalyptus* oil | 0.02 |
| Thickener and Viscosity Enhancer | Polyethylene Glycol | 0.01-0.1 |
| | Guar gum | 0.01-0.1 |
| Fragrance | Lavender oil | 0.5 |
| Moisturing and Wound Healing | Vitamin E | ≤0.02 |
| Freshness Handfeel | Frescolat ® MGA (Menthone Glycerin Acetal) | ≤0.02 |
| | Critic Acid (pH adjustment to PH = 5.5 to 6.5) | ≤0.02 |
| | Water | Balance to 100% |

Example 55

Hand Gel Sanitizer Formulation 7

Table 19 below shows a composition of a hand gel sanitizer formed from D1-thyme oil disinfecting capsules with lavender oil fragrance and vitamin E, and was prepared by mixing the listed components in sequence to obtain a water-based colloidal suspension.

TABLE 19

Hand Gel Sanitizer Formulation 7

| Component | Ingredient | Weight Percent |
|---|---|---|
| Antimicrobial Polymer | Polyethylenimine | 0.7 |
| | Polyhexamethylene biguanide | 0.1 |
| Stabilizer | Polyvinyl alcohol | 0.35 |
| Disinfectant | Thyme oil | 0.03 |
| Fragrance | Lavender oil | 0.03 |
| Skin-care | Vitamin E | 0.02 |
| Foam Stabilizer | Tween ® 80 | 2.5 |
| Foamer | Sodium dodecyl sulfate | 2.5 |
| Moisturing and Wound Healing | Sodium hyaluronic | ≤0.02 |
| Emollient | Cetyl alcohol | ≤0.02 |
| Vitamin and Antioxidant | Vitamin C | ≤0.02 |
| Freshness Handfeel | Frescolat ® MGA (Menthone Glycerin Acetal) | ≤0.02 |

Example 56

Hand Gel Sanitizer Formulation 8

Table 20 below shows a composition of a hand gel sanitizer formed from D1-thyme oil disinfecting capsules with lavender oil fragrance and vitamin E, and was prepared by mixing the listed components in sequence to obtain a water-based colloidal suspension. The bactericidal tests were carried out on $10^5$ CFU *E. coli E. coli* at 60 seconds contact.

TABLE 20

Hand Gel Sanitizer Formulation 8

| Component | Ingredient | Weight Percent |
|---|---|---|
| Antimicrobial Polymer | Polyethylenimine | 0.7 |
| Stabilizer | Polyvinyl alcohol | 0.35 |
| Disinfectant | Cinnamaldehyde (cinnamon) | 0.03 |
| Thickener and Viscosity Enhancer | Glycerin | 0.01-0.1 |
| | Guar gum | 0.01-0.1 |
| | Critic Acid (pH adjustment to PH = 5.5 to 6.5) | ≤0.02 |
| | Water | Balance to 100% |

It is to be understood that the hand sanitizer and method of making the same is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A hand foam sanitizer, comprising:
at least one foaming agent;
at least one stabilizing agent;
at least one skin care agent;
at least one freshness agent comprising menthone glycerin acetal; and
a volume of disinfecting capsules suspended in the at least one foaming agent, the at least one stabilizing agent, the at least one skin care agent, and the at least one freshness agent, wherein each said disinfecting capsule comprises a polymer shell having a core, the polymer shell comprising an antimicrobial material,
wherein the at least one stabilizing agent comprises at least one foam stabilizer having a concentration of 2.5 wt % of the hand foam sanitizer,
wherein the at least one skin care agent has a concentration less than or equal to 0.04 wt % of the hand foam sanitizer, and
wherein the menthone glycerin acetal has a concentration less than or equal to 0.02 wt % of the hand foam sanitizer.

2. The hand foam sanitizer as recited in claim 1, wherein the core of each said disinfecting capsule is selected from the group consisting of a hollow core, a core comprising at least one disinfectant, a core comprising at least one fragrance, a core comprising at least one supplemental skin care agent, and combinations thereof.

3. The hand foam sanitizer as recited in claim 1, wherein the at least one foaming agent is adapted for producing a foam by air foaming.

4. The hand foam sanitizer as recited in claim 3, wherein the at least one foaming agent and the at least one stabilizing agent are each adapted to maintain a size and shape of the foam for at least 60 seconds at room temperature.

5. The hand foam sanitizer as recited in claim 4, wherein the at least one foaming agent is selected from the group consisting of soap, liquid soap, powdered detergent, liquid detergent, sodium dodecyl sulfate, a surfactant, and combinations thereof.

6. The hand foam sanitizer as recited in claim 5, wherein the at least one stabilizing agent is selected from the group consisting of a nonionic surfactant, an emulsifying agent, polysorbate 20, polysorbate 40, polysorbate 80, and combinations thereof.

7. The hand foam sanitizer as recited in claim 1, wherein the at least one skin care agent is selected from the group consisting of at least one moisturizer, at least one skin repair agent, at least one emollient, at least one vitamin, and combinations thereof.

8. The hand foam sanitizer as recited in claim 1, wherein the at least one skin care agent is selected from the group consisting of hyaluronic acid, sodium hyaluronic, vitamin E, ceramides, sodium PCA, glycerin, glycerol, silicones, petrolatum, salicylic acid, alpha hydroxy acids, vitamin C, hyaluronic acid, beta-glucan, shea butter, mineral oil, plant butter, cocoa butter, lanolin, petrolatum, paraffin, beeswax, squalene, cetyl alcohol, triethyhexanoin, vitamin A, vitamin D, vitamin K, vitamin B3, vitamin B5, choline, and combinations thereof.

9. The hand foam sanitizer as recited in claim 1, wherein the antimicrobial material has a concentration of between 0.5 wt % and 95 wt % of the polymer shell.

10. The hand foam sanitizer as recited in claim 9, wherein the polymer shell comprises at least one polymer selected from the group consisting of anionic polymers, cationic polymers, nonionic polymers and combinations thereof.

11. The hand foam sanitizer as recited in claim 9, wherein the polymer shell comprises at least one polymer selected from the group consisting of primary amines, secondary amines, tertiary amines, zwitterionics, quarternary ammoniums, polyethylenimine, polyquaternium, polyhexamethylene biguanide, poly(diallyldimethylammonium chloride, functionalized chitosan and combinations thereof.

12. The hand foam sanitizer as recited in claim 1, wherein the core of each said disinfecting capsule comprises at least one disinfectant selected from the group consisting of alcohol, chlorhexidine, antimicrobial phytochemicals, antimicrobial essential oils, agarwood oil, cajuput oil, cananga oil, cinnamon bark oil, citronella oil, clove oil, eucalyptus oil, fennel oil, ginger oil, kaffir lime oil, nutmeg oil, ollium xanthorrhiza oil, origanum oil, patchouli oil, rosemary oil, sandalwood oil, tea tree oil, thyme oil, vetiver oil and combinations thereof.

13. The hand foam sanitizer as recited in claim 1, wherein the core of each said disinfecting capsule comprises at least one fragrance selected from the group consisting of essential oils of flowers, essential oils of fruits, essential oils of aromatic woods and combinations thereof.

14. The hand foam sanitizer as recited in claim 1, wherein the core of each said disinfecting capsule comprises at least one supplemental skin care agent selected from the group consisting of hyaluronic acid, sodium hyaluronic, vitamin E, ceramides, sodium PCA, glycerin, glycerol, silicones, petrolatum, salicylic acid, alpha hydroxy acids, beta-glucan, mineral oil, plant butters, shea butter, cocoa butter, lanolin, petrolatum, paraffin, beeswax, squalene, cetyl alcohol, triethyhexanoin, vitamin A, vitamin C, vitamin E, vitamin D, vitamin K, vitamin B3, vitamin B5, choline, catechins and combinations thereof.

15. A method of making a hand foam sanitizer, comprising the step of selectively mixing a skin care ingredient-containing solution with a suspension, wherein the skin care ingredient-containing solution comprises at least one skin care agent having a concentration less than or equal to 0.04 wt % of the hand foam sanitizer, and wherein the suspension comprises:
    at least one foaming agent;
    at least one stabilizing agent comprising at least one foam stabilizer having a concentration of 2.5 wt % of the hand foam sanitizer;
    at least one freshness agent comprising menthone glycerin acetal, wherein the menthone glycerin acetal has a concentration less than or equal to 0.02 wt % of the hand foam sanitizer; and
    a volume of disinfecting capsules suspended in the at least one foaming agent, the at least one stabilizing agent and the at least one freshness agent, wherein each said disinfecting capsule comprises a polymer shell having a core, the polymer shell comprising an antimicrobial material.

* * * * *

UNITED STATES PATENT AND TRADEMARK OFFICE
CERTIFICATE OF CORRECTION

| | | |
|---|---|---|
| PATENT NO. | : 11,517,510 B2 | |
| APPLICATION NO. | : 16/518154 | |
| DATED | : December 6, 2022 | |
| INVENTOR(S) | : King Lun Yeung, Ying Li and Ning Zhan | |

It is certified that error appears in the above-identified patent and that said Letters Patent is hereby corrected as shown below:

On the Title Page

Item (73) please insert the first Assignee as --CHIAPHUA INDUSTRIES LIMITED, Hong Kong (CN)--, and the second Assignee being listed as --GERMAGIC BIOCHEMICAL TECHNOLOGY (SHANGHAI) CO., LTD. Shanghai (CN)--.

Signed and Sealed this
Thirty-first Day of January, 2023

Katherine Kelly Vidal
*Director of the United States Patent and Trademark Office*